United States Patent
Szente et al.

(10) Patent No.: US 6,432,928 B1
(45) Date of Patent: Aug. 13, 2002

(54) COMPLEXES AND THEIR COMPOSITIONS

(75) Inventors: Lajos Szente; Jozsef Szejtli; Maria Vikmon nee Kiraly; Julia Szeman, all of Budapest (HU)

(73) Assignee: Chinoin Gyogyszer es Vegyeszeti Termekek Gyara Rt., Budapest (HU)

( * ) Notice: Subject to any disclaimer, the term of this patent is extended or adjusted under 35 U.S.C. 154(b) by 0 days.

(21) Appl. No.: 08/836,390

(22) PCT Filed: Nov. 2, 1995

(86) PCT No.: PCT/HU95/00055

§ 371 (c)(1),
(2), (4) Date: Aug. 1, 1997

(87) PCT Pub. No.: WO96/14872

PCT Pub. Date: May 23, 1996

(30) Foreign Application Priority Data

Nov. 11, 1994 (HU) ............................................. 9403237

(51) Int. Cl.$^7$ ......................... A61K 31/715; C08B 37/16
(52) U.S. Cl. .......................................... 514/58; 536/103
(58) Field of Search .............................. 536/103; 514/58

(56) References Cited

U.S. PATENT DOCUMENTS

| 4,826,963 A | * | 5/1989 | Stadler Nee Szoke et al. | 536/103 |
| 5,180,716 A | * | 1/1993 | Yaksh et al. | 514/58 |

FOREIGN PATENT DOCUMENTS

| AU | B 61835/94 | 5/1994 |
| EP | 605753 | * 7/1994 |

OTHER PUBLICATIONS

Internal Medicine, 4th Edition, Editor–in–Chief Jay Stein, Chapters 71–72, pp. 699–715.*
Scrip No. 2434/35.

* cited by examiner

Primary Examiner—James O. Wilson
Assistant Examiner—Everett White
(74) Attorney, Agent, or Firm—Birch, Stewart, Kolasch & Birch, LLP

(57) ABSTRACT

This invention provides inclusion complexes of Taxol ((2aR-(aα,4β,4αβ,6β,9α(αR*,βS*),11α,12α,12aα,12bα))-β-(benzoylamino)-α-hydroxy-benzene-propanoic acid 6,12-b-bis(acetyloxy)-12-(benzoyloxy)-2a,3,4,4a,5,6,9,10,11,12, 12a,12b-dodecahydro-4,11-dihydroxy-4a,8,13,13-tetramethyl-5-oxo-7,11-methano-1H-cyclo-deca-(3,4)-benz-(1,2-b)-oxeth-9-yl-ester)) or Taxotere (butoxycarbonyl-10-desacetyl-N-debenzoyl-Taxol) or Taxus extracts formed with a cyclodextrin derivative and a co-solvent. This invention relates to pharmaceutical composition with increased water-solubility and stability. This invention provides the process for the preparation of an inclusion complex of Taxol or Taxotere or a brevifolia extract of Taxus formed with a cyclodextrin derivative and a co-solvent. This invention relates to pharmaceutical composition, containing as active ingredient an effective amount of an inclusion complex of Taxol or Taxotere or a Taxus brevifolia extract formed with a cyclodextrin derivative, preferably heptakis-2,6-0 dimethyl-β-cyclodextrin, random methylated β-cyclodextrin, succinylmethyl-β-cyclodextrin and a co-solvent together with usual filling, diluting and other auxiliaries generally used in the pharmaceutical industry.

22 Claims, 2 Drawing Sheets

COMPLEXES AND THEIR COMPOSITIONS

The invention relates to the inclusion complexes or mixtures of Taxol {[2aR-[2aα,4β,4αβ,6β,9α(αR*, βS*a11α,12α,12aα,12bα]]-β-(benzoylamino)-α-hydroxy-benzene-propanoic acid 6,12-b-bis(acetyloxy)-12-(benzoyloxy)-2a,3-4,4a,5,6,9,10,11,12,12a,12b-dodecahydro-4,11-dihydroxy-4a,8,13,13-tetra-methyl-5-oxo-7,11-methano-1H-cyklodeca[3,4]-benz-[1,2-b]-oxeth-9-yl-ester]} or Taxotere (butoxycarbonyl-10-desacetyl-N-debenzoyl-Taxol) or Taxus extracts (containing other diterpene Taxane derivatives besides Taxolon like cephalomannin 10-desacetyltaxol, desacetyl-baccatine III, baccatine III, baccatine III, cinnamoyl taxines, taxusine) formed with a cyclodextrin derivative and a co-solvent, process for their preparation and pharmaceutical compositions containing them, further their pharmaceutical application.

Although Taxol shows promising biological effect and significant anti-tumor activity, its pharmaceutical use is accompanied by several difficulties:

- the solubility of taxanes is rather poor, e.g. taxol dissolves in water at 25° C. by 0.55–0.59 µg/ml (determined by Cyclolab Kft. Budapest);
- taxol is very sensitive to light and pH, during its decomposition biologically inactive products are formed;
- the pharmacological results relating to taxol are questionable because the solvents used (Cremophor EL) are themselves cytotoxic [J. N. Denis; J. Am Chem. Soc. 110, 5917 (1988); M. I. Fjaellskog et al: Lancet. 342–873 (1993); and L. Webster et al: J. Natl. Cancel Inst. 85, 1685 (1993)].

Several processes are known for eliminating the disadvantageous features described above:

- use of solubilizing agents [1:1 mixture of Cremophor EI and anhydrous ethanol (Natl. Cancer Institute, Paclitaxel Documentation)];
- forming of chemically modified micromicelles by using phosphatidylethanolamines (Lipis Specialities, Inc., European patent specification No. 118.316);
- use of ethanol polysorbate mixtures for increasing solubility (Rhone-Poulenc Rorer, European patent specifications Nos. 522.936 and 522.937);
- use of liposomic taxol formulations [e.g. R. Aquilar and R. Rafaelloff: published patent specification No. WO 93/18751; A. Sharma et al: Pharm. Res. 11, 889–896 (1994); and M. H. Alkan et al: J. Liposome Research 3.42 (1993)]: a Taxol concentration of about 1 mg/ml was obtained in unstable (four days at room temperature) compositions.

Attempts have been made for increasing the water-solubility of taxol also by forming synthetic derivatives [Zhao et al: J. Nat Prod. 54, 6, 1607 (1991); D. I. Kingston and Y. Y. Xang: European patent specification No. 537.905 and H. M. Deutsch et al: U.S. Pat. No. 5,157,0049]. The biological effectiveness of the chemically modified taxol derivatives having increased water-solubility was, however, modified disadvantageously, the multidrug resistance showed generally an increasing tendency while cytotoxicity, i.e. the biological effect, decreased.

To overcome the difficulties connected with the parenteral administration of taxol, taxol prodrugs with increased water-solubility have also been synthetized [A. Matthew et al: J. Med. Chem. 35, 1, 145 (1992)].

Bartoli et al tried to improve the generally weak stability of taxol by its microencapsulation [H. Bartoli et al: J. Microencapsulation, 7, 2, 191, (1991)].

Especially the preparation of liquid taxol-containing pharmaceutical compositions for parenteral administration is difficult as the diterpenoid-type, very lipophilic taxane derivatives cannot be converted into suitable storable solutions in the desired concentration even by using significant amounts of detergents and mixtures containing aqueous-organic solvents [D. Tarr et al: Pharm. Res. 4, 162–165 (1987)]. The taxol composition described contains soybean oil, lecithin, egg-yolk, phosphilipids and glycerol, its taxol-content is, however, only 0.3 mg/ml due to the low solubility. A taxol emulsion with a taxol content of 20 mg/ml has also been developed; this composition contains 50% of triacetine (1,2,3-triacetyl-glycerol) but this triacetine has also been proved toxic (in mouse experiments $LD_{50}$=1.2 mg/ml, a 50% triacetine emulsion).

The registered parenteral taxol compositions are formulated in emulsions in a concentration of 6 mg/ml containing a 1:1 by volume mixture of polyoxyethylated castor oil (Cremophor-EL): alcohol and are diluted to ten-fold volume when administered. The use of these parenteral compositions is accompanied by several disadvantageous side effects such as a heavy allergy due to the Cremophor EL administered intravenously. Further, the taxol formulations prepared in an ethanolic solvent mixture are not clear solutions but are slightly opalescent [L. A. Trissel: Am. J. Hosp. Pharm. 50, 300 (1993)], thus they can precipitate when diluted or administered simultaneously with other medicines.

The only commercially available Taxol composition, i.e. PACLITAXEL (prepared by the firm Bristol-Myers-Squibb), contains 6 mg/ml of Taxol together with 527 mg/ml Cremophor EL and 47% by weight of anhydrous ethanol. Before administration it is to be diluted by 0.9% physiologic sodium chloride solution of 5% dextrose to a concentration of 0.03 mg/ml. The physical and chemical stability of the diluted solution is indicated between 12 and 24 hours. The diluted solution must be filtered through a 0.2µmembrane filter before its administration by infusion as the solution may be opalescent due to the non-ionic surfactants, such as Cremophor EL.

Although the Cremophor EL generally used in Taxol derivatives is well soluble and is a solvent generally used in the preparation of other pharmaceutical compositions, it is not a biologically inert agent. It causes sensitivity reactions accompanied by different vasodilating, air-thirst causing and hypotensive effects. According to literature references [e.g; Pharmacology and Toxicology of Cremophor EL diluent: The Annals of Pharmacotheraphy, 1994 May, Vol. 28, S11–S115; Pharmaceutical Research, Vol. II., No. 6, 889–895; and Vol. II, No. 2, 206–212, (1994)] Cremophor EL is toxic and causes allergic reactions. Its toxic effect has been proved also by our own biological pharmacological tests. The Journal of the National Cancer Institute (Vol. 85, No. 20, Oct. 20, 1993) describes that Cremophor EL is not only toxic but in case of Taxol compounds inhibits the active ingredients to exert their effect in the intracellular field.

A mixed-miceller proliposomal Taxol composition suitable for parenteral administration is described by H. A. Onynksel et al (Pharm. Res. Vol. 11, No. 2, 206–212). Taxol is dissolved in a mixed micelle system containing bile acid salt and phospholipide and the spontaneously formed liposomes are diluted. The solubility of Taxol can be increased only to 0.8 mg/ml even by using various bile acid salts (sodium desoxycholate, sodium cholate, sodium taurocholate, sodium taurodesoxycholate).

According to the authors the large-scale production is connected with plenty of problems and the stability of the composition is limited as Taxol is precipitated upon standing. A slight precipitation is declared in case of a composition containing 0.4 mg/ml of Taxol stored at a temperature of 7 to 24° C. The composition is diluted directly before administration. Mouse tests prove that bile acid salts are less toxic than Cremophor EL.

In patent specification No. WO 94/07484 published recently (Research Corporation Technologies Inc., USA) Taxol-containing solutions and emulsions are disclosed. Taxol is dissolved in alcohol, then in oil and oil-in-water type emulsions containing 0.5–5 mg/ml of Taxol and having a drop size of 2–10 μm are prepared. These compositions are, however, unsuitable for administration by injection or infusion.

In patent specifications Nos. WO 94/12030 and WO 94/12198 injectable Taxol compositions are disclosed. In order to increase their stability, the pH-value of the Taxol and Cremophor EL containing compositions is adjusted to a value below 8.1, preferably between 5 and 7.5 by citric acid (the pH-value of the know Paclitaxel is 9.1) to obtain a solution with a stability of 7 days at 40° C.

In Australian patent specification No. 645,927 (Ensuiko Sugar Refining Co. Ltd. Yokohama-Shi, Japan) the inclusion complexes of Taxol formed with α- and γ-cyclodextrin further with maltosyl derivatives of cyclodextrins are disclosed, 1 mole of Taxol is reacted with 1–20 moles of cyclodextrin or a derivative thereof. The authors describe that the solubility of Taxol is increasing. The solubility increasing effect of γ-cyclodextrin proved to be the best at an increasing extent by increasing the concentration, however, only a solubility of 0.16 mg/ml could be achieved at a molar ratio of 1:20.

The interaction between 23 anticancer agents, Taxol included, and hydroxypropyl-β-cyclodextrin has been studied by T. Cserháti et al (Int. J. Pharm., 1994, 108,1, 69–75) and it was found very low in case of Taxol.

As disclosed in our Hungarian patent application No. P93 01373 we aimed at increasing the solubility of Taxol and Taxol derivatives by using cyclodextrins and derivatives thereof. A solubility of about 1 mg/ml could be achieved by using in each case 250–350 moles of a methylated cyclodextrin derivative related to 1 mole of Taxol. A complex has also been prepared from 1 mole of Taxol by using 2.3 moles of DIMEB in solid phase.

From the aforesaid it follows that according to literature references a Taxol concentration of up to about 1 mg/ml can be achieved by the various methods, except for the compositions prepared by using Cremophor EL (e.g. PACLITAXEL, 6 mg/ml). These are, however, not acceptable due to the toxic character of Cremophor EL.

The present inventors had the aim to increase the water-solubility of Taxol, Taxotere and Taxus extracts to a Taxol concentration of about 3–6 mg/ml without using Cremophor EL, which is a toxic auxiliary generally used in Taxol compositions. Further, we set the aim to prepare stable pharmaceutical compositions which can be diluted and formulated according to the different administration methods.

According to our invention the solubility of Taxol, Taxotere and Taxane derivatives is increased by using cyclodextrins and/or cyclodextrin derivatives and/or mixtures thereof and co-solvents without forming a real chemical bond between the Taxol type compounds and cyclodextrins. Depending on the mole ratios used and reaction conditions, solubility increasing interactions arise or complexes are formed with increased solubility. The formed inclusion complexes may optionally be recovered. The increase of the solubility achieved may be further increased by using a co-solvent and due to the use of co-solvents even compositions of such a concentration may be obtained which can be diluted by water without risking precipitation or decomposition.

The solubility-increasing effect of co-solvents is a surprising recognition as according to B. W. Müller and E. Albers (Journal of Pharmaceutical Sciences, Vol. 80, No. 6, June 1991) co-solvents disadvantageously influence the solubility-increasing effect of cyclodextrin derivatives. They examined and found disadvantageous the effect of the usual solubilizing agents, such as 1,2-propyleneglycol, sodium desoxycholate, exerted on different active ingredients (e.g. cholesterol) and hydroxypropyl-β-cyclodextrin.

The positive and synergistic effect of ethanol for increasing the solubility of Taxol with the simultaneous use of cyclodextrin was surprising as several earlier publications declared that the solubilizing effect of the chemically modified cyclodextrins is decreased by ethanol even in low concentrations M. Otagiri et al described [Acta Farm. Suec. 1984, 21(6), p. 357–366] that the value of the stability constant and thereby the achievable solubility-increasing effect in the case of β-cyclodextrin and methylated derivatives is linearly decreased by methanol. In case of flufenamic acid the measurements indicated that the "aqueous" stability constant decreased from 1300 $M^{-1}$ to about 400 $M^{31\ 1}$ in the presence of 25% by volume methanol.

J. Pitha and T. Hoshino [Int. J. Pharm., 80,243 (1992)] and T. Loftsson et al [7th Int. Symp. on Cyclodextrin (1994), Tokyo] also report that the drug-cyclodextrin complex formation decreases on the effect of different adjuvants, such as organic solvents. For example, in aqueous medium the solubility-increasing effect of cyclodextrin testosterone is decreased by ethanol even in low concentration, it acts as a competitive "guest" molecule.

In our experiments we have found that although a similar decrease was expected from ethanol, an increase of activity and an improvement of absorption could be observed.

Although Taxol itself dissolves well in ethanol and in a 1:1 mixture of ethanol and water, it immediately precipitates when diluted.

In our experiments we have found in case of a higher concentration, i.e. 4–6 mg/ml of Taxol and 150–200 mg/ml DIMEB or RAMEB (molar ratio of 1:10–1:20) that a clear solvent is obtained in a 1:1 or 2:1 co-solvent mixture of ethanol and distilled water. This mixture became cloudy during storage, then the Taxol precipitated and the solvent turned to white and gelatinous. However, on adding either an alcohol or a cyclodextrin derivative or mixtures thereof, the stable solution state could be reinstated.

We have further recognized that the best solubility could be observed at a Taxol:cyclodextrin molar ratio of about 1:30–1:40, when cyclodextrin presumably induces not only the interaction necessary for the complex-formation but further, e.g. hydrotropic interactions.

The compositions which contain Taxol and a cyclodextrin derivative and are prepared with a co-solvent, are clear solutions without opalescence and can be stored at room temperature by normal light for three months and can be, if necessary, further diluted. Thus, they can be used also in the form of injections and infusions.

Thus, the present invention relates to inclusion complexes of Taxol {[2aR-[2aα,4β,4αβ,6β,9α(αR*,βS*),11α-12α,12aα,12bα]] β-(benzoylamino)-α-hydroxy-benzene-propanoic acid 6,12-b-bis(acetyloxy)-12-(benzoyloxy)-2a,3,4,4a,5,6,9,10,11,12,12a,12b-dodecahydro-4,11-dihydroxy-4a,8,13,13-tetramethyl-5-oxo-7,11-methano-1H-cyclo-deca

[3,4]-benz-[1,2-b]-oxeth-9-yl-ester]} or Taxotere (butoxycarbonyl-10-desacetyl-N-debenzoyll-Taxol) or Taxus extracts formed with a cyclodextrin derivative and a co-solvent.

Further, the present invention relates to compositions of increased water-solubility and stability, containing 0.01–0.6% by volume of a Taxol or Taxotere or Taxus extract, 10–65% by volume of cyclodextrin derivative, 10–90% by volume of a co-solvent and water in an amount necessary to 100% by volume.

The inclusion complexes of the invention can be prepared by a) reacting a Taxol or Taxotere or Taxus extract in an aqueous co-solvent mixture with a cyclodextrin derivative, then separating the complex from the mixture by a method known per se;

b) reacting a Taxol or Taxotere or Taxus extract with a co-solvent and a cyclodextrin derivative in solid phase;

c) subjecting a Taxol or Taxotere or Taxus extract, a cyclodextrin derivative and a co-solvent to "high energy milling" treatment.

The complex can be separated from the mixture e.g. by filtration, centrifuging, lyophilization, drying by pulverization or drying in vacuo.

The "high energy milling" treatment of a Taxol or Taxotere or Taxus extract with a cyclodextrin derivative is disclosed in the published Hungarian patent specification No. T/52.366.

As preferred cyclodextrin derivatives the following compounds may be used:

heptakis-2,6-0-dimethyl-β-cyclodextrin (DIMEB);

random methylated β-cyclodextrin (RAMEB);

succinyl-methyl-β-cyclodextrin (SUMEB);

2-hydroxypropyl-β-cyclodextrin (HO-P-βCD); and soluble anionic β-cyclodextrin polymer (CDPSI).

As co-solvent ethanol or a mixture of ethanol and water, preferably a (1–10):1, more preferably (1–3):1 mixture of ethanol and water can be used. The Taxol, Taxotere or Taxus extract and cyclodextrin were used in a molar ratio of 1:(10–65), preferably 1:(30–40).

The solubility-increase of Taxol was examined in the presence of cyclodextrins and derivatives thereof by the Higuchi-Connor method (Advances in Analytical Chemical Chemistry and Instrumentation, Vol. 4, New York, Willey-Interscience 1965, p. 117–212).

Aqueous solutions containing cyclodextrins in different, increasing concentrations, aqueous co-solvents-containing mixtures and Taxol in an amount higher than can be dissolved, were stirred at 22° C. for 24 hours (this time proved to be enough for complete dissolution). The suspension was filtered through a membrane filter with a pore size of 0.2–0.4 μm, and by diluting the clear filtrate the Taxol concentrations were measured by high pressure liquid chromatography method [HPLC, J. Leslie et al: J. Pharm. and Biomed. Anal 11, 1349 (1993)].

The water-solubility of Taxol was measured without cyclodextrin in the presence of different cyclodextrin derivatives by using co-solvents. The results are summarized in Table 1. The solubility data show that the solubility already increased due to the presence of cyclodextrins was further increased by the co-solvent.

TABLE 1

| CD | solubility mg/ml | molar ratio TAXOl:CD | co-solvent | remark |
|---|---|---|---|---|
| — | 0.0059 | | water | |
| — | 4 | | 2:1 ethanol:water | clear solution. opalescening. then white precipitate |
| γ-CD | 4 | 1:63 | 2:1 ethanol:water | white suspension |
| DIMEB | ~1 | 1:250 | water | |
| | 4 | 1:30 | 2:1 ethanol:water | |
| RAMEB | 0.0044 | 1:1500 | water | |
| | 0.0425 | 1:750 | water | |
| | 0.2317 | 1.300 | water | |
| | 0.8599 | 1:278 | water | |
| | 4 | 1:33.8 | 2:1 ethanol-water | |
| | 4 | 1;35 | ethanol-water | |
| OH-P-βCD | 0.1 | 1:28#5 | water | |

When preparing pharmaceutical compositions for the treatment of human cancer we selected, on the basis of the measured solubility data, solutions with relatively high Taxol that are stable and can be diluted by water without opalescence.

The effect of the Taxol-cyclodextrin compositions was examined on two human cancer cell cultures (PC 3 and K 562) in Taxol concentrations corresponding to a Taxol content of $10^{-4}$, $10^{-5}$ and $10^{31\ 6}$ moles.

The examined compositions were the diluted solutions of Taxol-DIMEB according to Example 1, Taxol-RAMEB according to Example 2 and Taxol-γ-cyclodextrin according to Example 4. As control solutions containing similar amounts of cyclodextrins and no Taxol, further the Taxol-Cremophor EL composition. Cremophor EL solution and the untreated cell cultures were examined.

The experiments were carried out and evaluated on both cell lines according to the examination methods of F. Skehan et al [New Colorimetric Assay of Anticancer Drug Screening, J. Natl. Canc. Inst. 82, 1107–1113 (1990) and A. Martin and M. Clynes (Comparison of 5 Microplate Colorimetric Assays for in Vitro Cytotoxicity Testing and Cell Proliferation Assays, Cytotechnology 11, 49–58 (1993)] in the Pathological and Experimental Cancer Research Institute No. 1 of the Semmelweis Medical University, Budapest.

The cells were exposed in a RPMI 1640 medium containing 10% of Foetal Calf Serum (FCS) medium on a microplate of 96 wells, by placing 5000 cells in 100 μl of medium.

The cell cultures were treated after 24 hours with a solution containing the test substances in 100 μl of a FCS-free RPMI medium, thus the final concentration of FCS became 5%. Every evaluation point is the averaged result of 8 parallels, the control was present in 8 parallels on each plate, thus the evaluation point was obtained by averaging 24 parallels. The eight test compositions were examined simultaneously, in one test on each cell line.

After 72 and 96 hours the cell growth was measured by SRB-assay (the determining method is SRB-painting of the total protein, the total protein is proportional to the cell growth, the extinction was read by a Microplate reader at a wave length of 540 nm).

During the tests both cell lines were in growing phase even in the last 24 hours. The test results are summarized in Tables 2 and 3. From the data obtained it follows that:

Cremophor EF proved to be toxic per se for both tested cell lines;

cyclodextrins in a concentration of 0.1 mM without taxol (highest concentration used) caused practically a total cell destruction;

in case of the most diluted concentration (0.001 mM) the cyclodextrin "carriers" proved to be ineffective, they did not hinder proliferation. The Taxol-γ-cyclodextrin showed some effect in case of cell line PC 3, while the Taxol-DIMEB and Taxol-RAMEB compositions showed a higher cytotoxicity both on cell lines K 562 and PC 3 than the corresponding cyclodextrin derivative alone;

in case of cell line PC 3 the cytotoxic effect of Taxol-cyclodextrin was at least as high as that of Taxol dissolved in Cremophor EL.

TABLE 2

The effect of $10^{-6}$M of Taxol and cyclodextrin on cell line PC 3

| Cell line PC 3 | Incubation Time | |
|---|---|---|
| | 72 hours | 96 hours |
| control | 0.757 ± 0.204 (100%) | 1.320 ± 0.298 (100%) |
| Cremophor EL | 0.544 ± 0.134 (72%) | 0.911 ± 0.280 (69%) |
| Taxol-Cremophor EL | 0.189 ± 0.079 (25%) | 0.279 ± 0.080 (21%) |
| γ-CD | 0.582 ± 0.126 (77%) | 0.937 ± 0,214 (71%) |
| Taxol-γ-CD | 0.254 ± 0.069 (34%) | 0.255 ± 0.063 (19%) |
| DIMEB | 0.725 ± 0.200 (96%) | 1.345 ± 0:269 (102%) |
| Taxol-DIMEB | 0.404 ± 0.097 (53%) | 0.228 ± 0.038 (17%) |
| RAMEB | 0.701 ± 0.174 (93%) | 1.496 ± 0.217 (113%) |
| Taxol-RAMEB | 0.196 ± 0.054 (26%) | 0,154 ± 0.032 (12%) |

Cremophor is slightly toxic in the tested concentration.
Taxol-Cremophor is more toxic than Cremophor.
DIMEB and RAMEB are not toxic in the tested concentrations.
In Taxol-DIMEB and Taxol-RAMEB mixtures the cytotoxic effect of Taxol previal.
γ-CD is slightly toxic to the cells per se, the toxic effect of the Taxol-γ CD mixture is higher than that of γ-CD.

TABLE 3

The effect of 10–6M of Taxol and cyclodextrin on cell line K562

| Cell line K562 | Incubation Time | |
|---|---|---|
| | 72 hours | 96 hours |
| control | 1.109 ± 0.235 (100%) | 1.571 = 0.336 (100%) |
| Cremophor EL | 0.556 ± 0.237 (50%) | 0.836 ± 0.158 (50%) |
| Taxol-Cremophor EL | 0.459 ± 0.094 (41%) | 0.394 ± 0.058 (25%) |
| γ-CD | 0.555 ± 0.200 (50%) | 0.531 ± 0,072 (34%) |
| Taxol-γ-CD | 0.448 ± 0.070 (40%) | 0.606 ± 0.107 (39%) |
| DIMEB | 0.819 ± 0.178 (74%) | 1.729 ± 0.185 (110%) |

TABLE 3-continued

The effect of 10–6M of Taxol and cyclodextrin on cell line K562

| Cell line K562 | Incubation Time | |
|---|---|---|
| | 72 hours | 96 hours |
| Taxol-DIMEB | 0.383 ± 0.075 (35%) | 0.513 ± 0.064 (33%) |
| RAMEB | 0.922 ± 0.239 (83%) | 1.696 ± 0.163 (108%) |
| Taxol-RAMEB | 0.196 ± 0.054 (26%) | 0,154 ± 0.032 (12%) |

Cremophor is toxic in the tested concentration.
Taxol-Cremophor is more toxic than Cremophor.
DIMEB and RAMEB are not toxic in the tested concentrations.
In Taxol-DIMEB and Taxol-RAMEB mixtures the cytotoxic effect of Taxol previal.
γ-CD is very toxic to the cells, the toxic effect of the Taxol-γ-CD mixture is not stronger than that of γ-CD.

The present invention also relates to pharmaceutical compositions which a) contain an effective amount of an inclusion complex of a Taxol or Taxotere or Taxus brevifolia extract formed with a cyclodextrin derivative, preferably heptakis-2,6-0-dimethyl-β-cyclodextrin, random methylated β-cyclodextrin, succinylmethyl-β-cyclodextrin and a co-solvent, as active ingredient together with filling, diluting and further auxiliaries generally used in the pharmaceutical industry;

b) contain an effective amount of Taxol or Taxotere or a Taxus brevifolia extract and a cyclodextrin derivative, preferably heptakis-2,6-0-dimethyl-β-cyclodextrin, random methylated β-cyclodextrin, succinylmethyl-β-cyclodextrin and a co-solvent, as active ingredient together with filling, diluting and further auxiliaries generally used in the pharmaceutical industry;

c) contain an inclusion complex of Taxol, Taxotere or Taxus extracts formed with a cyclodextrin or a cyclodextrin derivative as active ingredient, they further contain ethanol or an ethanol-water mixture.

The pharmaceutical compositions described above can be prepared by methods known per se.

The pharmaceutical compositions can be used for treating human cancer by administering an effective amount of a pharmaceutical composition containing an inclusion complex of Taxol or Taxotere or a Taxus extract with a cyclodextrin derivative, preferably heptakis-2,6-0-dimethyl-β-cyclodextrin, random methylated β-cyclodextrin, succinylmethyl-β-cyclodextrin and a co-solvent.

The treatment of human cancer can also be performed by administering an effective amount of a pharmaceutical composition containing as active ingredient Taxol or Taxotere or a Taxus extract and a cyclodextrin derivative, preferably heptakis-2,6-0-dimethyl-β-cyclodextrin, random methylated β-cyclodextrin, succinylmethyl-β-cyclodextrin and a co-solvent.

The advantages of the compositions according to the invention are as follows:

they are pharmaceutical compositions containing an effective amount of a Taxol or Taxotere or Taxus extracts, they contain besides the Taxol active ingredients less amount of cyclodextrin derivative than expected due to the effect of the co-solvent, the amount and side-effect of the "carriers" deminished;

the Taxol compositions were prepared without using Cremophor EL;

stable solutions were prepared containing 3–6 mg/ml of Taxol, Taxotere or Taxus extract, which can be diluted by water without limitation, thus they can be used also for injection of infusion purpose;

the solutions containing 3–6 mg/ml of Taxol, Taxotere or Taxus extracts are stable at room temperature at normal daylight for three months and show no opalescence or precipitation within 8 hours even in diluted state.

In another embodiment of the invention, the present invention relates to a pharmaceutical composition with increased water-solubility and stability containing Taxol or Taxotere or a Taxus extract containing 0.01–0.6% by weight of Taxol or Taxotere or a Taxus extract;
10–65% by weight of a cyclodextrin derivative;
10–90% by weight of a co-solvent; and
water in an amount necessary to 100% by weight.

Figure 1A:
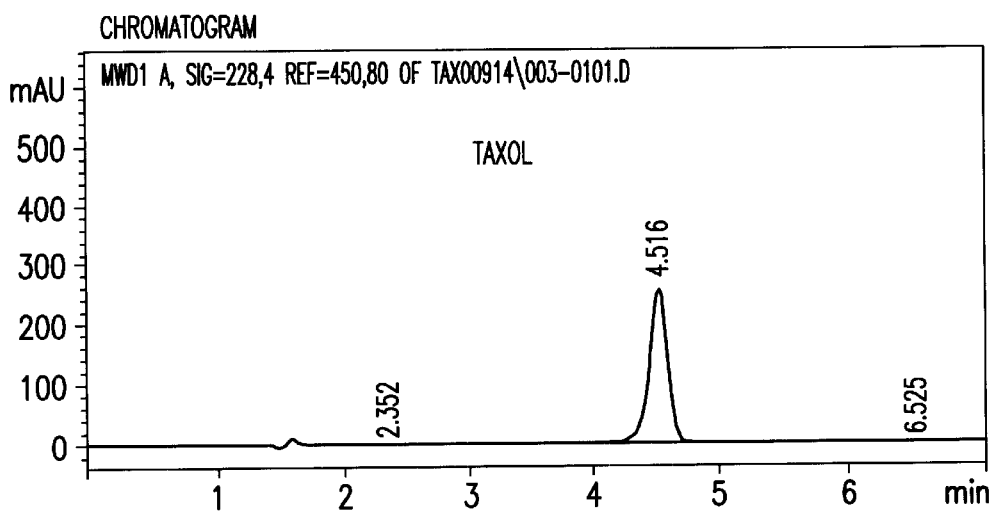
FIGS. 1A, 1B and 1C show the comparative HPLC chromatograms of the Taxol-DIMEB and RAMEB formulations prepared according to Examples 1 and 2 after a two-month storage at room temperature by light.
Figure 1B:
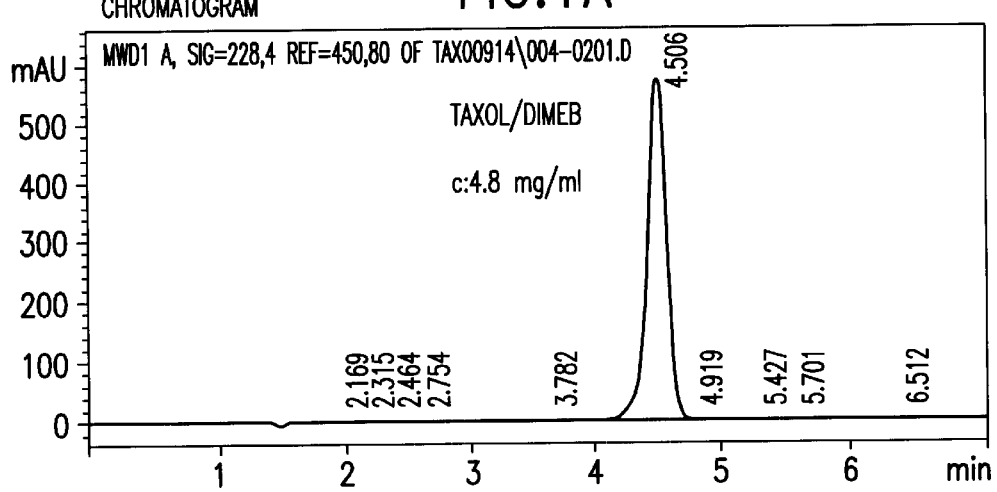
Figure 1C:
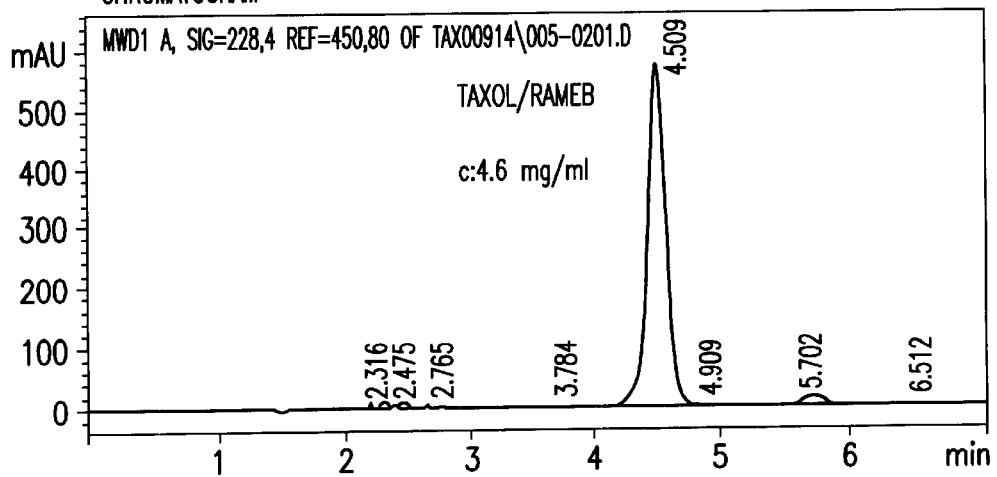
Figure 2:
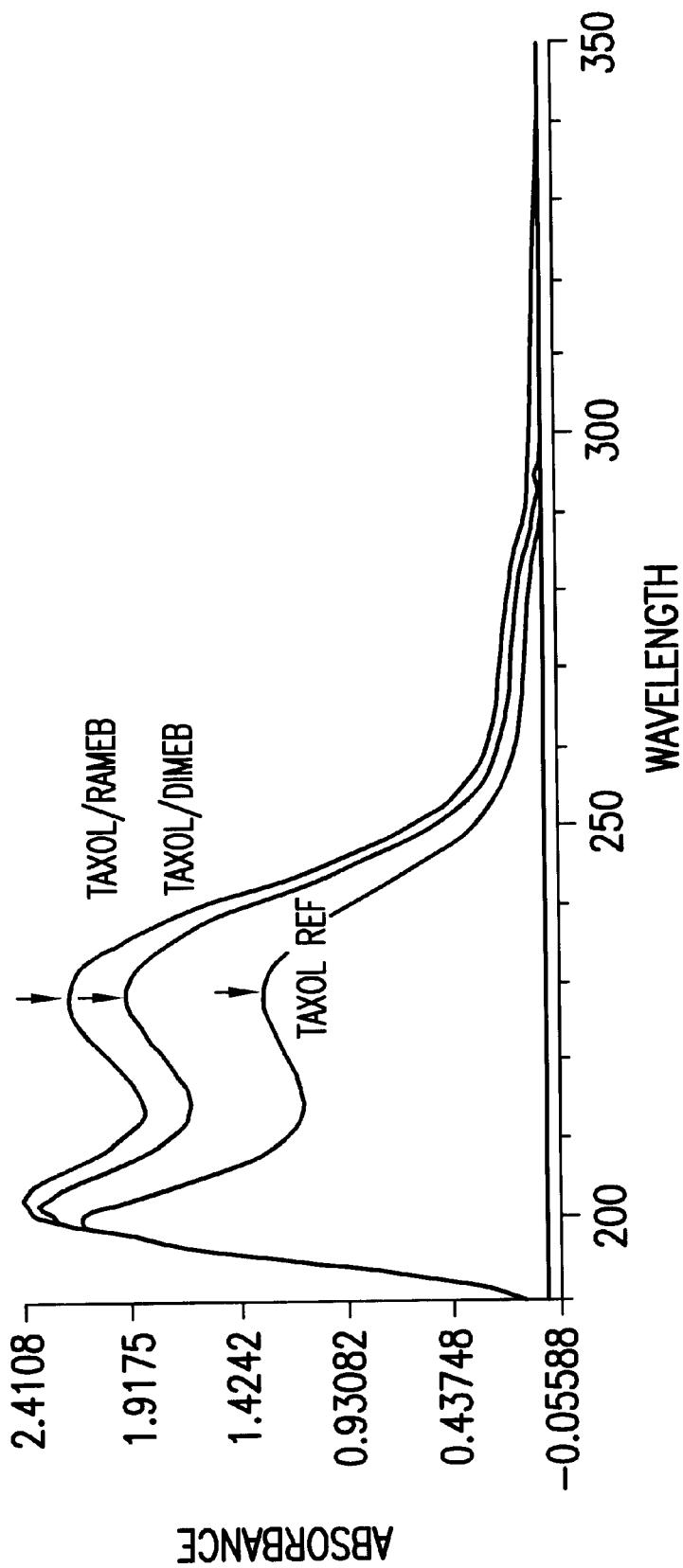
FIG. 2 shows the ultraviolet spectra of the same formulations also after storage.

In both cases the comparative compound is the freshly made Taxol reference solution.

the compositions containing the Taxol, Taxotere or Taxus extract showed cytotoxicity on the PC 3 and K 562 human cancer cell lines.

The details of the invention are illustrated by the following non-limiting examples.

EXAMPLE 1

A Taxol-DIMEB composition containing 4 mg/ml of Taxol 8.7 mg of Taxol (prepared by SIGMA, St. Luise, USA) are dissolved in 1.3 ml of 95% ethanol by ultrasonic stirring, then 400 mg of DIMEB and 0.6 ml of water are added. The solution is homogenized and stirred by ultrasound till the solution becomes clear. A stable, dilutable solution is obtained.

EXAMPLE 2

A Taxol-DIMEB composition containing 4 mg/ml of Taxol 8.6 mg of Taxol are dissolved in 1.3 ml of 95% ethanol, 400 mg of RAMEB (prepared by Wacker Chemie GmbH. München, Germany) and 0.6 ml of distilled water are added. The solution is homogenized by ultrasonic stirring and clear solution is obtained.

EXAMPLE 3

A Taxol-DIMEB composition is prepared by dissolving 3.7 mg of Taxol and 200 mg of RAMEB simultaneously in 0.7 ml of 95% of ethanol. After stirring and complete dissolution also a clear solution is obtained, the Taxol content of which is 5.1 mg/ml.

EXAMPLE 4

4.0 mg/ml of Taxol and 100 mg/ml γ-cyclodextrin are dissolved in a 2:1 mixture of ethanol and water. A white suspension is obtained after homogenization and ultrasonic stirring.

EXAMPLE 5

A solution containing 3 mg/ml of Taxotere 2.5 mg of Taxotere was dissolved in 0.5 ml of 95% ethanol. 175 mg of DIMEB and 0.3 ml of water are added. After ultrasonic stirring a clear solution is obtained.

EXAMPLE 6

A composition containing 5 mg/ml of Taxol 2.7 mg of Taxol are dissolved in 0.35 ml of 95% ethanol. 250 mg of RAMEB and 0.15 ml of water are added. After stirring a clear solution is obtained.

EXAMPLE 7

The Taxol-DIMEB composition according to Example 1 is stored in ampoules at room temperature for 3 months. An infusion solution is prepared for treating human cancer by diluting the content of each ampoule to its 100fold with distilled water, 1.9% isotonic saline solution and 5% dextrose solution. A clear solution is obtained in the case of all the three dilutions which did not change according to visual observation in 6 hours after dilution (no opalescence, no precipitation). According to HPLC control the active ingredient content of the solutions did not change during storage.

EXAMPLE 8

The Taxol-DIMEB solution according to Example 1 is diluted to its 100fold volume by 0.9% physiologic saline solution containing 5 mg/ml of DIMEB. A diluted solution is obtained which can be stored for 48 hours without opalescence.

EXAMPLE 9

The Taxol-RAMEB solution according to Example 2 is diluted to its 100fold volume with 5% dextrose solution containing 5 mg/ml of RAMEB. A stable, clear solution is obtained which can be stored for 48 hours.

What is claimed is:

1. An inclusion complex of Taxol or Taxotere with increased water-solubility and stability formed with a heptakis-2,6-0-dimethyl-β-cyclodextrin and either ethanol or a mixture of ethanol and water.

2. An inclusion complex of Taxol or Taxotere with increased water-solubility and stability formed with random methylated β-cyclodextrin and either ethanol or a mixture of ethanol and water.

3. An inclusion complex of Taxol or Taxotere with succinylmethyl-β-cyclodextrin and either ethanol or a mixture of ethanol and water and having increased water-solubility and stability.

4. Inclusion complexes of Taxol ((2aR-(aα,4β,4αβ,6β,9α (αR*,βS*)11α-12α,12aα.12bα))-β-(benzoylamino)-α-hydroxy-benzene-propanoic acid 6,12-b-bis(acetyloxy)-12-(benzoyloxy)-2a,3,4,4a,5,6,9,10,11,12,12a,12b-dodecahydro-4,11-dihydroxy-4a,8,13,13-tetramethyl-5-oxo-7,11-methano-1H-cyclodeca(3,4)-benz-(1,2-b)-oxeth-9-yl-ester)) or Taxotere (butoxycarbonyl-10-desacetyl-N-debenzoyl-Taxol) formed with ethanol or a mixture of ethanol and water and with a cyclodextrin derivative selected from the group consisting of heptakis-2,6,O-dimethyl-β-cyclodextrin (DIMEB), random methylated β-cyclodextrin (RAMEB), and succinylmethyl-β-cyclodextrin (SUMEB).

5. An inclusion complex according to claim 4, which comprises a 1:1–10:1 mixture of ethanol and water.

6. An inclusion complex according to claim 4, which comprises a 1:1–3:1 mixture of ethanol and water.

7. An inclusion complex according to claim 4, wherein the molar ratio of Taxol or Taxotere to cyclodextrin is 1:10–1:65.

8. An inclusion complex according to claim 4, wherein the molar ratio of Taxol or Taxotere to cyclodextrin is 1:30–1:40.

9. A pharmaceutical composition containing as an active ingredient an effective amount for increasing water solubility and stability of an inclusion complex of Taxol or Taxotere formed with a cyclodextrin derivative selected from the group consisting of heptakis-2,6,0-dimethyl-β-cyclodextrin, random methylated β-cyclodextrin, and succinylmethyl-β-cyclodextrin, and a co-solvent of ethanol or a mixture of ethanol and water.

10. A pharmaceutical composition with increased water-solubility and stability containing Taxol or Taxotere comprising:

0.01–0.6% by weight of Taxol or Taxotere;

10–65% by weight of a cyclodextrin derivative selected from the group consisting of heptakis-2,6-O-dimethyl-β-cyclodextrin (DIMEB), random methylated β-cyclodextrin (RAMEB), and succinylmethyl-β-cyclodextrin (SUMEB);

10–90% by weight of ethanol or a mixture of ethanol and water; and optionally water or a suitable carrier in an amount necessary to obtain 100% by weight.

11. The composition according to claim 10, wherein the molar ratio of Taxol or Taxotere to cyclodextrin is 1:10–1:65.

12. The pharmaceutical composition according to claim 10, which comprises a 1:1–10:1 mixture of ethanol and water.

13. The pharmaceutical composition according to claim 10, which comprises a 1:1–3:1 mixture of ethanol and water.

14. The pharmaceutical composition according to claim 10, wherein the molar ratio of Taxol or Taxotere to cyclodextrin is 1:30–1:40.

15. The pharmaceutical composition of claim 10, which comprises about 3–6 mg/ml of Taxol or Taxotere.

16. A process for inhibiting the division of cancer cells, which comprises treating a patient with an effective amount of the composition according to claim 10 for inhibiting division of said cancer cells.

17. A process for inhibiting the division of cancer cells, which comprises treating a patient with an effective amount of an inclusion complex of Taxol or Taxotere formed with ethanol or a mixture of ethanol and water and with a cyclodextrin derivative selected from the group consisting of heptakis-2,6,O-dimethyl-β-cyclodextrin (DIMEB), random methylated β-cyclodextrin (RAMEB), and succinylmethyl-β-cyclodextrin (SUMEB), for inhibiting division of said cancer cells.

18. A process according to claim 17, wherein the treatment is orally or parenterally.

19. The process of claim 17, wherein the effective amount is 3–6 mg/ml.

20. A process for inhibiting the division of cancer cells, which comprises treating said cancer cells with an effective amount of an inclusion complex of Taxol or Taxotere formed with ethanol or a mixture of ethanol and water with a cyclodextrin derivative selected from the group consisting of heptakis-2,6,O-dimethyl-β-cyclodextrin (DIMEB), random methylated β-cyclodextrin (RAMEB), and succinylmethyl-β-cyclodextrin (SUMEB), for inhibiting division of said cancer cells.

21. The process of claim 20, wherein the effective amount is 3–6 mg/ml.

22. A process for the preparation of an inclusion complex of Taxol or Taxotere formed with either ethanol or a mixture of ethanol and water and with a cyclodextrin derivative, which comprises reacting Taxol or Taxotere with a cyclodextrin derivative selected from the group consisting of heptakis-2,6,O-dimethyl-β-cyclodextrin (DIMEB), random methylated β-cyclodextrin (RAMEB), and succinylmethyl-β-cyclodextrin (SUMEB), and ethanol or a mixture of ethanol and water.

* * * * *